United States Patent [19]

Marsan

[11] 4,326,521
[45] Apr. 27, 1982

[54] APPLIANCE FOR THE TREATMENT OF COLOSTOMY AND THE LIKE

[76] Inventor: Arthur E. Marsan, 240 Ferrari Ct., El Paso, Tex. 79912

[21] Appl. No.: 125,344

[22] Filed: Feb. 28, 1980

Related U.S. Application Data

[63] Continuation-in-part of Ser. No. 728,517, Nov. 11, 1976, abandoned.

[51] Int. Cl.³ .............................................. A61F 5/44
[52] U.S. Cl. ................................................... 128/283
[58] Field of Search ................................ 128/283, 295

[56] References Cited

U.S. PATENT DOCUMENTS

| | | | |
|---|---|---|---|
| 2,224,773 | 12/1940 | Shaulson | 24/198 X |
| 2,604,096 | 7/1952 | Smith | 128/283 |
| 2,782,785 | 2/1957 | Arcand | 128/283 |
| 2,837,094 | 6/1958 | Cowles | 128/283 |
| 3,076,458 | 2/1963 | Mason | 128/283 |
| 3,100,488 | 8/1963 | Orowan | 128/283 |
| 3,557,790 | 1/1971 | Hauser | 128/283 |
| 3,789,846 | 2/1974 | Barrett et al. | 128/283 |
| 3,825,005 | 7/1974 | Fenton | 128/283 |
| 3,898,990 | 8/1975 | Wolan | 128/283 |

*Primary Examiner*—Michael H. Thaler
*Attorney, Agent, or Firm*—John F. McCanna

[57] ABSTRACT

This invention provides modified forms of an improved appliance for the treatment of colostomy and the like designed to be manufactured at a low cost and to be economical and advantageous to the user. The appliance is unique in that it has a gasket molded in a single operation to form a unitary structure having plural portions which have different functions. The pouch has a receiving end and a drain end. One plural portion of the gasket forms a snap-ring hinged to the gasket when the gasket is molded and adapted to be moved by hand on its hinge to connect the receiving end of the pouch to the gasket at the outlet end of the stoma opening. Another portion of the gasket forms means for locking the drain end of the pouch to the gasket. At each opposite side of the gasket another portion has openings for threading the ends of a belt to the gasket to hold the appliance on a patient. In a modified form of the appliance one plural portion forms a diaphragm extending diametrically across the stoma opening forming the rear wall of a compartment for gel. This feature serves to extend the time between the application of fresh gel and extends the life of the appliance. Also, it serves to prevent excoriation of abdominal skin around the stoma and makes for a more satisfactory appliance. Another feature provides novel means for connecting the drain end of a tubular pouch to the gasket.

1 Claim, 15 Drawing Figures

U.S. Patent  Apr. 27, 1982  Sheet 1 of 3  4,326,521
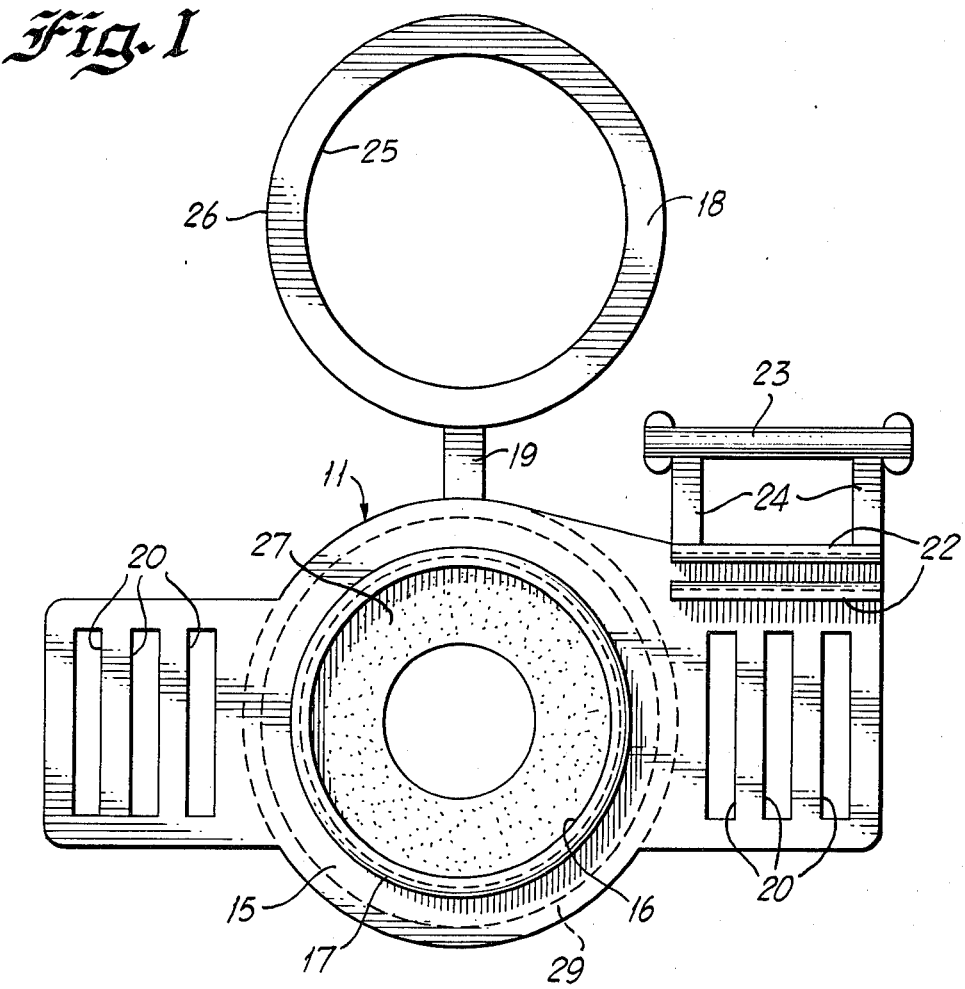
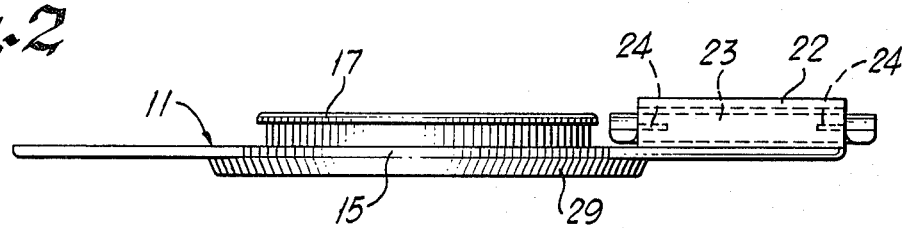
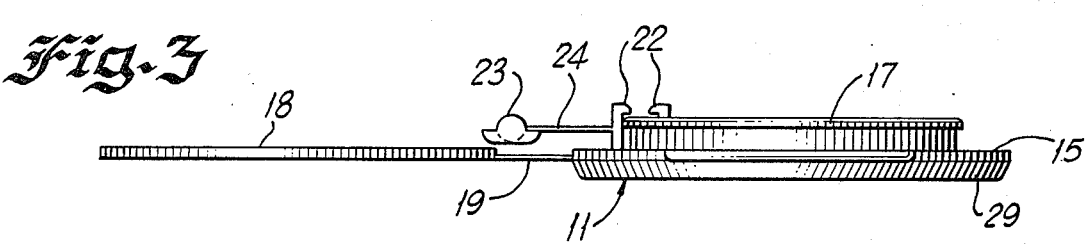
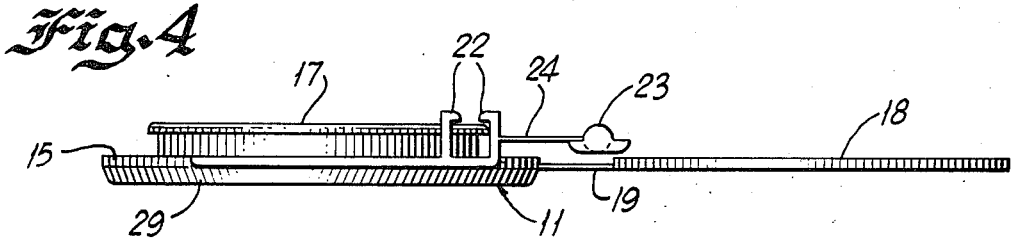

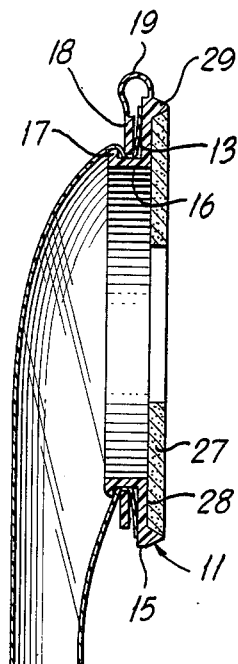
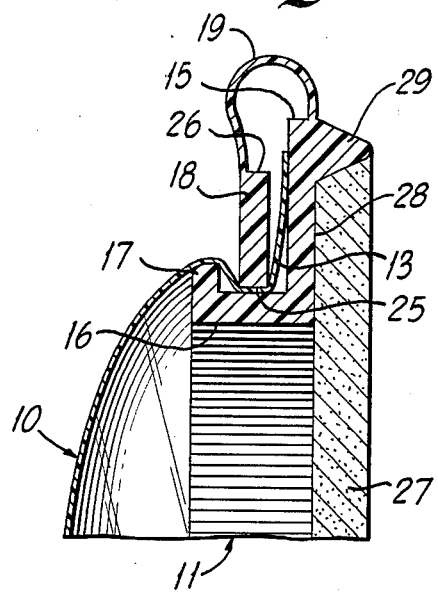
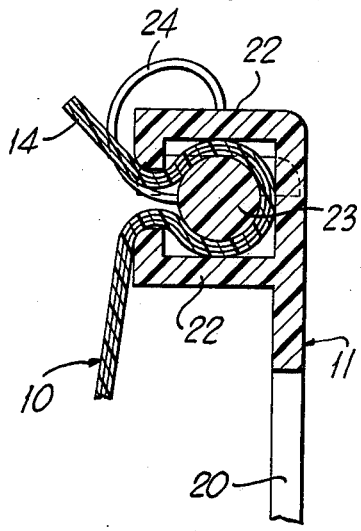
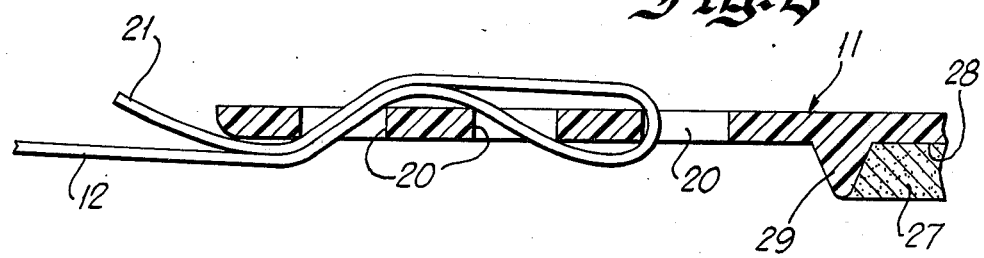
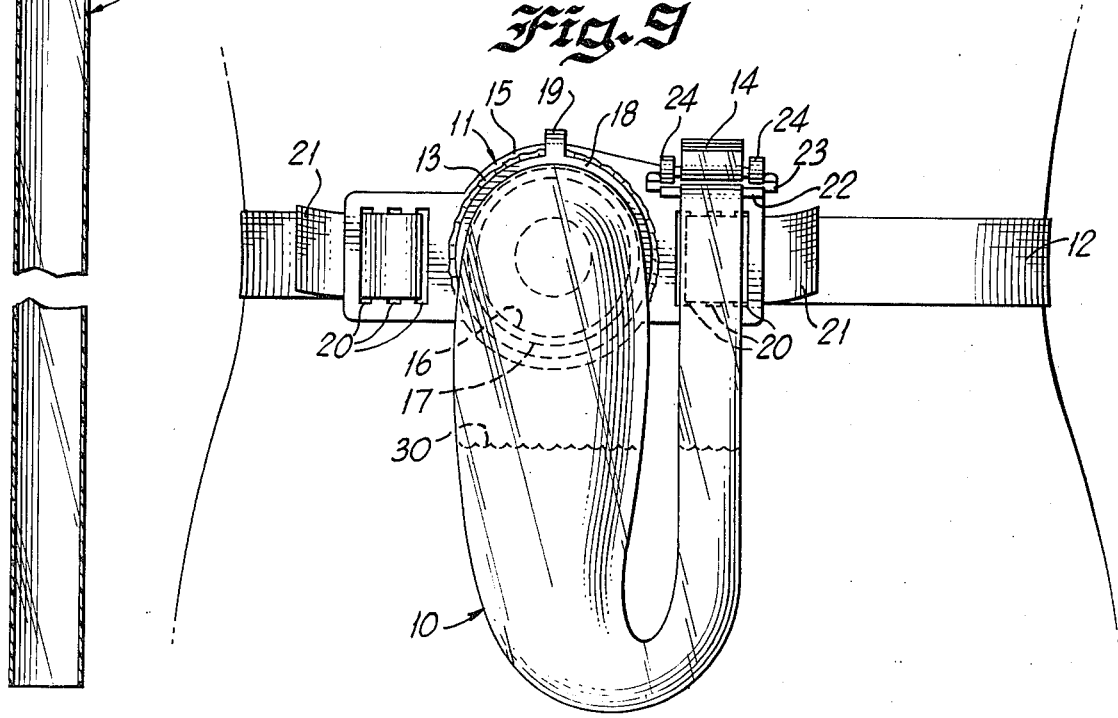

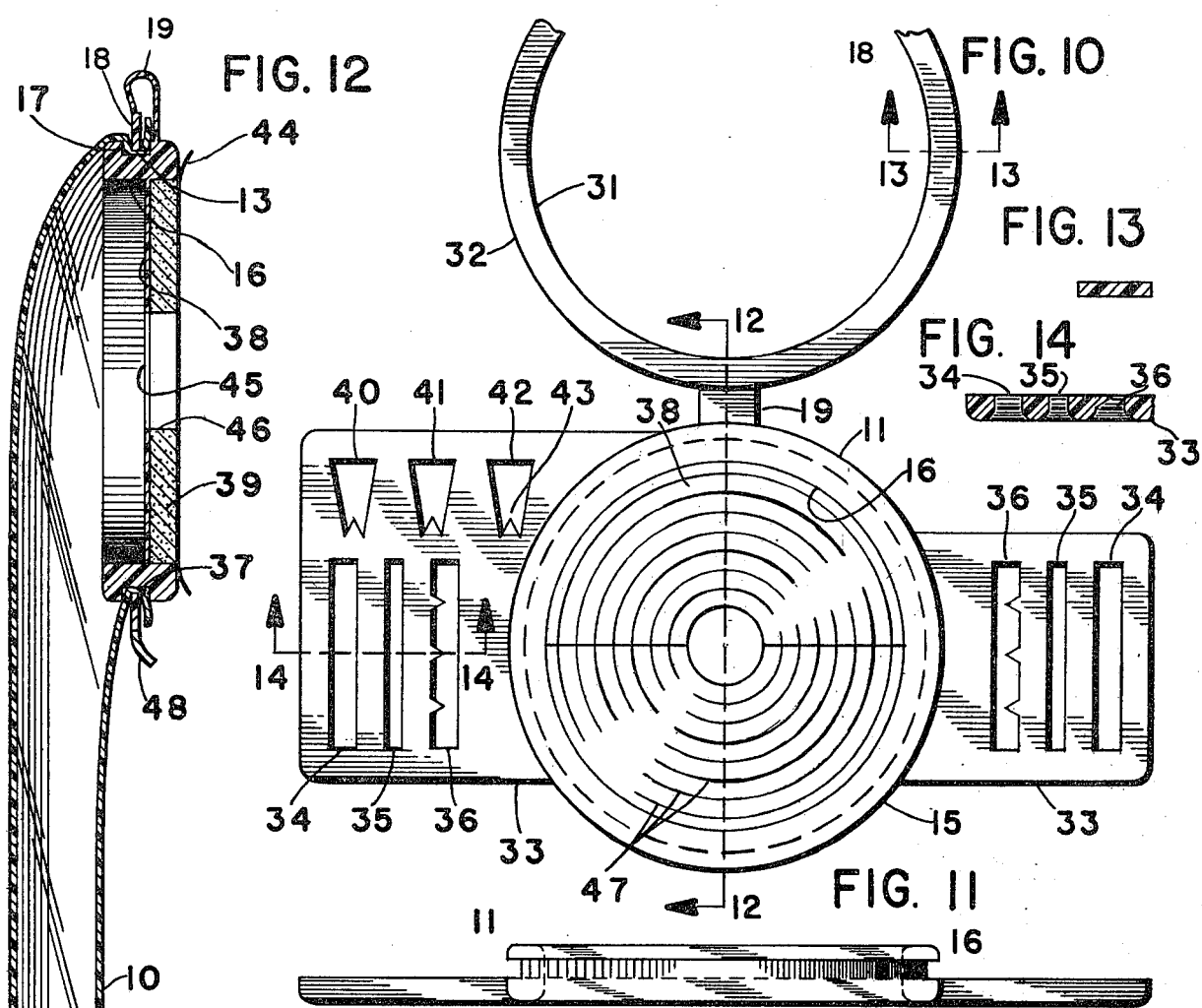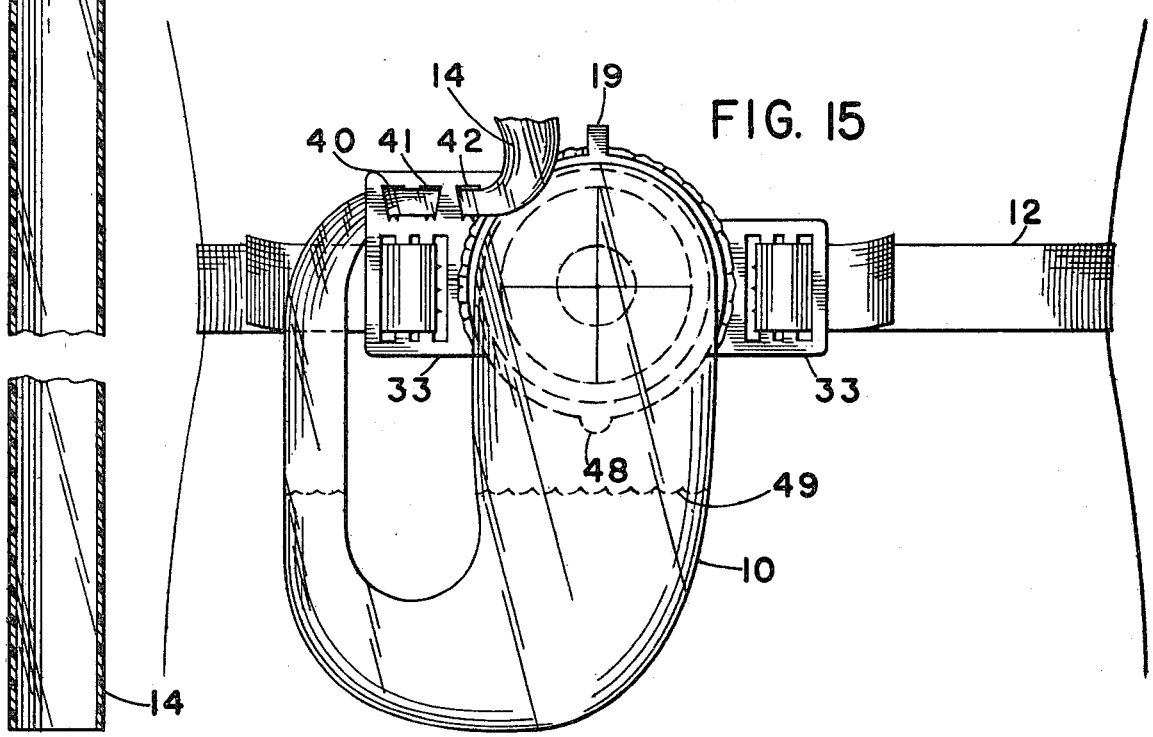

APPLIANCE FOR THE TREATMENT OF COLOSTOMY AND THE LIKE

This is a continuation-in-part application based on my application for patent Ser. No. 728,517, filed Nov. 11, 1976, now adandoned entitled IMPROVED APPLIANCE FOR THE TREATMENT OF COLOSTOMY AND THE LIKE, and includes all subject matter disclosed and claimed in my application Ser. No. 728,517.

BACKGROUND OF THE INVENTION

The present invention is the result of applicant's association with the treatment of colostomy continuously over a period upward of 40 years. His father had colostomy for 17 years. Applicant made many inventions in this art during this period and was granted 14 United States patents and was also engaged in the manufacture and sale of colostomy appliances.

This invention provides an improved appliance comprising only three components, a pouch for receiving the fecal discharge from the stoma, a gasket of unique construction, and a belt for holding the appliance on a patient. The gasket is unique in that it is molded in a single operation to form a unitary structure having plural portions which have different functions serving all the requirements of the appliance without the use or need of extra or extraneous parts or devices.

The term "ostomy" has come into use to define, in a broad sense, the surgical procedures known as colostomy, ileostomy, cecostomy, ureterostomy, ileal conduct, ileal bladder, wet colostomy, etc. This surgery usually results in an artificial opening through the abdominal wall for the terminal end of the intestine or duct called a stoma to discharge the body wastes of feces or urine. Many devices have been developed through the years to aid in the treatment of ostomy patients, but none has been suitable for all patients. This is due to the lack of satisfactory appliances and to the differences in surgical techniques and the physiological condition of patients.

In a broad sense, the problem facing most patients is to collect the fecal discharge from the stoma in some kind of container without restricting the patient's general activities. A specific problem encountered by many patients is to prevent the discharge from contacting the skin surrounding the stoma as it can cause excoriation of the skin which is painful. Heretofore, face plates of appliances have been cemented to the skin to prevent excoriation but they are only useful for a limited time. Karaya gel seals have been used in an effort to eliminate the problem of excoriation; however, karaya is not satisfactory. Some of the objections are the high cost of karaya seals and the relatively short life due to the water solubility of karaya. Another objection is that the karaya gel seals do dry out and become hard and brittle on the dealer's shelves awaiting to be sold. When gel seals absorb moisture from the discharge they swell and can cause strangulation of the stoma and restrict the discharge flow. These conditions are very unsatisfactory. Furthermore, the time required to remove a gel seal and clean the area with repeated washing with soap and water and drying thoroughly before reapplication of skin preparations which can be most objectionable. And face plates that have been cemented on the skin with waterproof adhesives must be removed periodically and usually organic solvents must be applied to remove residual adhesive that remains on the skin. Organic solvents are not benefitial to the skin as they remove natural oils; also they are costly, have a bad odor, are usually inflamable, and are very time consuming.

The present invention overcomes the above objections to the high cost of kayaya gels, water solubility, strangulation of the stoma, excoriation of the skin, loss of time, and the use of adhesives and organic solvents.

The invention provides an appliance of novel construction incorporating many functions and advantages which overcome the objections to prior devices.

Referring to the drawings:

FIG. 1 shows in flat form a gasket at the time of molding and before it is applied to a patient;

FIG. 2 is an edge view of the gasket looking at the front edge;

FIG. 3 is an edge view of the gasket looking at the opposite edge;

FIG. 4 is an edge view of the gasket looking at the right hand edge of FIG. 1;

FIG. 5 is an enlarged vertical section through the appliance as it is assembled for application to a patient;

FIG. 6 is a further enlarged vertical section through the upper portion of the section shown in FIG. 5;

FIG. 7 is an enlarged section showing the attachment of the drain end of the pouch to the gasket;

FIG. 8 shows one end of the belt threaded through slots in a portion of the gasket for connecting the belt thereto;

FIG. 9 is a diagramatic view illustrating application of the appliance to a patient;

FIG. 10 shows in flat form a gasket in another embodiment of my invention, at the time of molding and before it is applied to a patient;

FIG. 11 is a front edge view of the gasket shown in FIG. 10;

FIG. 12 is an enlarged vertical section taken on the section line 12—12 of FIG. 10 showing the pouch connected to the gasket;

FIG. 13 is a section taken on the section line 13—13 of FIG. 10;

FIG. 14 is a section taken on the section line 14—14 of FIG. 10; and

FIG. 15 is a diagramatic view illustrating application of this form of the appliance to a patient.

In the preferred embodiment of my invention the appliance comprises three components, a pouch 10 for receiving the discharge from a patient, a gasket designated generally by 11 having integral therewith some unique features described hereinafter, and a belt 12 for holding the appliance on a patient. It will be noted, however, that some features of my invention may be used apart from said components, as will be noted in the claims.

The pouch is preferably of thin plastic tubing without seams. In the form of the pouch shown in FIG. 9 it has an open end 13 called a receiving end and an open end 14 called a drain end. The tubing may be of material between 0.001 and 0.010 of an inch in thickness. The gasket may be formed by any of various methods to produce the features shown and described herein. Preferably and most economically the gasket is molded to form a generally flat cylindrical body 15 having a central opening 16 for reception of the stoma. The gasket is molded to provide integral therewith an outwardly projecting lip 17 having an annular securing edge, a snap-ring 18 hinged at 19 to the gasket, two laterally spaced sets of slots 20 to receive by threading the ends of the belt 12, jaws 22 adapted to receive therebetween the drain end of the pouch, and a clamping bar 23 connected by hinges 24 to the gasket adjacent to the jaws and adapted to clamp and lock closed the drain end of the pouch between said jaws.

An important feature of my invention which makes for low cost of manufacture and other advantages which will be noted hereinafter, is the unique construction of the gasket. I accomplish this by molding in a single operation a unitary structure comprising a gasket body having a stoma opening and plural portions integral with the gasket body for performing different functions without the use of extra or extraneous parts. One such portion is the snap-ring 18 and its hinge 19, another the lip 17, another the jaws 22, another the clamping bar 23, another the gel cavity described below, and others the lateral extensions at the sides of the gasket body having slots 20 for threading the ends of the belt to the gasket body. All these portions perform separate and distinct functions and all are made a part of and integral with the gasket body. These plural portions are, therefore, in permanent and predetermined relation to the gasket body and also with respect to each other. This permanent relation of the parts serves to enable the desired and proper operating functions of these parts in the operation and use of my appliance. This feature distinguishes from prior appliances and devices for treating colostomy, because such prior appliances and devices require many manufactured parts some of which are of complicated construction which makes high cost of manufacture and high cost to the user.

Referring now to the use of my appliance. When applying the pouch to the gasket the receiving end of the pouch is inserted by hand into the center 25 in the snap-ring from the bottom at the right hand side thereof viewing FIG. 1. The leading annular end of this inserted end of the pouch is then folded by hand toward the outer edge of the snap-ring. The snap-ring is then moved by hand on the hinge 19 to position the open end of the pouch to the rear of the lip 17 in alignment therewith. The snap-ring together with the open end of the pouch is then moved forward by hand, snapping the ring with the pouch end over the lip to the position shown in FIGS. 5 and 6, thus securing the receiving end of the pouch to the gasket at the outlet end of the stoma opening.

The function of the snap-ring in its movement from its normal position at one side of the gasket when molded, shown in FIGS. 1, 3 and 4, to the position securing the pouch to the gasket, shown in FIGS. 5 and 6, is here described more in detail. The snap-ring has an inner annular edge 31 which is the center of the snap-ring and an outer annular edge 32. When the snap-ring is moved by hand on its hinge to the position shown in FIG. 5 it has been moved in a semi-circle, that is, a movement of about 180 degrees. In this hand movement of the snap-ring together with the receiving end of the pouch, the snap-ring is first moved rearwardly, that is, in a direction away from the inlet end of the stoma opening to a position at the rear of the lip 17, and then the snap-ring is moved forwardly to snap over the lip. It will be noted that the inner edge 31 which is of slightly smaller diameter than the outer periphery of the lip 17, compresses the interposed annular portion of the receiving end of the pouch between the snap-ring and the lip and in this action the snap-ring snaps over the lip to the position shown in FIGS. 5 and 6 and thereby secures the pouch to the gasket body.

After the appliance has been applied to a patient the drain end of the pouch will be folded by hand to a flat confined condition and placed across the opening between the jaws 22. The clamping bar 23 will then be moved by hand on its hinges to engage said drain end and force it between the jaws in a locking engagement shown in FIG. 7.

Before applying the appliance to a patient a gel seal 27 is placed in a cavity 28 formed by a retaining ring 29 at the stoma inlet side of the gasket molded integral therewith. The ring 29 prevents misalignment of the gel seal with respect to the gasket body and restrains outward flow of the gel when the appliance is on a patient. Since the gel is a tacky material which comes in contact with the abdomen for its sealing function, it is covered with a sheet release paper which is removed before placing the appliance on a patient.

When applying the appliance to a patient, usually one end of the belt is threaded through the slots 20 at the left side of the gasket as shown in FIG. 9. The gasket is then placed on the patient's abdomen with the stoma extending into the inlet end of the stoma opening 16. The other end of the belt is wrapped around the patient's waist and threaded through the slots 20 at the other side of the gasket and pulled snugly to hold the appliance on the patient. The drain end 14 of the pouch will then be locked to the gasket as described above so that the discharge will be collected in the pouch.

When the patient wishes to empty the collected discharge the patient stands adjacent to the toilet or positions a suitable container beneath the appliance. With one hand the patient grasps the drain end of the pouch below its connection to the gasket and above the discharge level and with the other hand grips the clamping bar and pulls outwardly to release the short drain end from the jaws. The hand holding the drain end of the pouch then directs the drain end so that the contents of the pouch drains into the toilet or a container if the patient is confined to bed. The pouch will then be washed and used again or a new pouch may be used if needed.

As above stated, the invention has many advantages. It enables low cost of manufacture. This economy is obtained by molding in a single operation a gasket body of unitary structure having plural portions which serve functions heretofore requiring many parts separate from and in addition to the gasket. This unitary gasket simplifies the handling of applicant's appliance and also simplifies the application of the appliance to a patient. It also avoids the loss or misplacement of parts such as belt buckles, slides, etc. for closing and locking the drain end of the pouch and miscellaneous parts and devices for connecting the receiving end of the pouch to the gasket. Heretofore such loose and separate parts were sometimes lost or misplaced or dropped in the toilet. This invention avoids this. In my invention all functioning parts are in permanent and predetermined relation to the gasket. This is effected by the snap-ring and the clamping bar being integrally hinged to the gasket body, also by the belt threading feature.

My invention also provides a modified embodiment shown in FIGS. 10 to 15. This embodiment is basically similar to the embodiment shown in FIGS. 1 to 9. The gasket in this embodiment is molded in a single operation forming a unitary structure having plural portions which have different functions. The reference numerals used in FIGS. 1 to 9 are used in FIGS. 10 to 15 when they apply to the same parts.

Referring now to FIGS. 10 to 15, this modification the same as in FIGS. 1 to 9, comprises three components, a gasket 11, pouch 10, and belt 12. The gasket here as well as that described above, is composed of any plastic or rubber material suitable for the needs of this invention, such for example as polyopylene, nylon, polyoinyl chloride, ABS, Hytrel, Saran, etc. The molding of this gasket is the same as described above. However, in the present embodiment the laterally extending portion 33 at each side of the gasket body is provided with slots 34, 35 and 36. The gasket body has an annular peripheral lip 17 at the outlet end of the stoma opening and a peripheral channel or groove 37 at the front of the lip as shown in FIG. 12. The pouch 10 has a receiving end 13 and a drain end 14. Another portion of the gasket body forms an annular snap-ring 18 hinged at 19 to the gasket body. Another portion forms a diaphragm 38 extending diametrically across the stoma opening intermediate the inlet and outlet ends of said opening, as shown in FIG. 12. All these portions are molded at one time integral with the gasket body. Each end of the belt is adapted to be threaded through the slots 34, 35 and 36 in one portion 33, as shown in FIG. 15. I have added teeth in the slot 36 which pierce each belt end, aiding to prevent it from pulling out. One portion 33 is provided with slots or openings 40, 41 and 42 each wide at the top with side walls narrowing to the bottom and having a pointed tooth 43 at the bottom, as shown in FIG. 10. These slots are adapted to receive the drain end 14 of the pouch inserted therein by hand, as shown in FIG. 15. This is for locking the drain end of the pouch to the gasket body and will be referred to more particularly below with reference to use of the appliance. This slotted portion may be applied to one or both sides of the gasket body to give accessibility to a left or right handed person using the appliance.

Referring to FIGS. 10 to 15, it will be noted that the diaphragm 38 forms the rear wall of a compartment which is filled with a gel 39. In this embodiment of my invention the gasket body is formed at its interior to provide said gel compartment as distinguished from the cavity 28 shown in FIGS. 5 and 6. The front end of this compartment is closed by a thin pull-off sheet 44. The gel compartment is of a capacity to hold a substantial quantity of gel. The compartment is filled with gel before the appliance is used, for example, at the factory where the appliance is manufactured. The pull-off sheet is applied at this time to close the compartment from loss of gel and for cleanness. The gel may be any of commercial gels now on the market, but other beneficial materials may be substituted for the commercial gels, such as petroleum jelly (Vasoline), or zinc oxide ointment, or Titanium dioxide. The larger amount of gel that can be placed around the stoma in the compartment the longer a patient can use the same gasket body. When the appliance is on a patient the stoma extends through an opening 45 in the center of the diaphragm. This opening is not in the diaphragm when the gasket body is molded, but it is to be cut in the diaphragm by hand using a scissors or sharp instrument just before the receiving end of the pouch is connected to the gasket body at the time of applying the appliance to a patient. At the same time the gel is opened at the center to receive the stoma. This permits a hot or cold liquid gel mixture to be filled in the compartment, which will solidify upon standing or cooling for a period of time. A larger opening may be cut in the center of the diaphragm to provide a snug fit around larger stomas. The intent is to have the discharge from the patient contact as little as possible of the gel. The diaphragm is about 0.002 to 0.005 of an inch in thickness. As shown in FIG. 10 there is a plurality of circular markings 46 on the diaphragm concentric with the center opening 45. These markings are guides for cutting the diaphragm to provide for larger stomas. Any suitable markings may be used. The diaphragm functions as the bottom of the compartment into which the gel is poured and solidifies. Another function of the diaphragm is that it protects the gel from disolving action of the stoma discharge when the appliance is on a patient.

Referring now to the feature of the tubular pouch and the connection of its drain end to the gasket. While my invention is not limited to sizes, the pouch shown in FIGS. 12 and 15 is preferably about 30 inches long and 4 inches in diameter. This is a preferred embodiment because it enables a great saving in cost to a patient. Heretofore, patients might use 1 to 10 pouches a day at a cost of 50 cents to 5 dollars a day. This preferred embodiment of pouch permits patients and hospitals to purchase pouch tubing in rolls from tubing manufacturers and cut off the pouches from the roll when needed. Also, the novel construction of the connection of the drain end of the pouch to the gasket described above, promotes low cost of manufacture of the appliance and in its simplicity it avoids the use of extra parts and unsatisfactory drain pouch connections heretofore used.

When the gasket body is in the condition at the time of molding shown in FIG. 10, the snap-ring is disposed at one side of the gasket body in a plane common therewith, as shown in FIGS. 3 and 4. The snap-ring is provided at its periphery with a tab 52 which serves as an aid to the user in finger gripping and manipulation of the snap-ring in connecting the pouch to the gasket body and removing it therefrom as described herein with reference to both modifications of the appliance. After the compartment has been filled with gel and the pull-off sheet applied, the receiving end 13 of the pouch will be inserted by hand from the bottom of the snap-ring upwardly through its center and this end of the pouch will be turned outwardly annularly over the snap-ring. The snap-ring will then be moved by hand on its hinge in an arc of 180 degrees, carrying with it the pouch, to position the snap-ring and pouch end at the rear of the lip 17, then moved by hand forwardly over the lip in a snap action to the position shown in FIG. 12, thus securing the receiving end of the pouch to the gasket body.

The appliance is thus assembled for application to a patient. One end of the belt will be connected to one portion 33, the pull-off sheet 44 will be removed, and the gasket body will be positioned on the abdomen of a patient with the stoma extending through the gel and the diaphragm. The other end of the belt will then be wound around the waist of the patient and connected to the other portion 33 to hold the appliance on the patient. The drain end 14 of the pouch will then be connected to the gasket body through the slot openings 40, 41 and 42 and the appliance is in operative position for use on the patient.

Referring to the described feature of the compartment in the gasket body having a large gel capacity, this serves to prevent excoriation of the skin around the stoma. It also serves to extend the time between the application of fresh gel seals. The gel seal gradually disolves and wastes away to be collected in the pouch with the discharge from the patient. The discharge will not disolve the plastic gasket body or the plastic pouch tubing. The gasket body and the pouch can be washed with soap and water when needed and fresh gel can be filled in the compartment when needed, for continued use of the appliance.

Referring again to the feature of connecting the drain end of the pouch to the gasket body. When the appliance has been belted to the patient the drain end will be connected to the gasket body. In doing this the terminal end of the drain end will be folded by hand into a compact condition and inserted into slot 40 from the bottom, then down through slot 41, and then up through slot 42, as shown in FIG. 15. The drain end is thus confined between the downwardly converging side walls of the slots and wedges by said side walls in the connection to the gasket body. After making this connection the drain end depending from the slots may be pulled down by hand to further the wedging engagement with the converging side walls of the slots and the teeth 43 at the bottom thereof. The weight of the discharge in the pouch also exerts a downward pull on the drain end and further insures against any disconnection of the drain end during use. Thus, without the use of buckles, slides and miscelaneous parts and devices, the drain end of the pouch is positively secured and locked to the gasket body with the drain end closed; and there is no danger of the drain end being loosened and pulled away and allowing flow of the discharge onto the patient and surroundings during use of the appliance. After the pouch has been filled with discharge from the patient, say to a level 49 shown in FIG. 15, the drain end will be withdrawn by hand from the slots to permit draining the discharge into a toilet or vessel and washing the pouch or applying a new pouch if needed.

Referring to the feature of the compartment having a large gel capacity, this serves to prevent excoriation of the abdominal skin around the stoma. It also serves to extend the time between the application of fresh gel seals. The gel gradually disolves and washes away to be collected in the pouch with the discharge from a patient. The discharge will not dissolve the plastic gasket body or the plastic pouch tubing.

In view of the novelty of my appliance and the different manual operations involved in using it, I will provide written intstructions to be included in the packaging of the appliance so that the buyer will be informed on how to properly use the appliance. And when it is considered that more than one million persons in the United States of America, aside from all foreign countries, are afflicted with colostomy and the like, it is believed that my invention will be appreciated by many such persons and that my appliance will provide improved means for treating this disease more economically and advantageously than with prior devices. Generally, the average life of a person who undergoes colostomy surgery is about an additional five years. As above mentioned, my father lived 17 years after colostomy surgery. This was due to the special and excellent care we gave to him. My present invention was conceived as the result of the many years of my experience in the treatment of colostomy and in developing and patenting improved means for treating colostomy. I believe the use of my appliance by persons afflited with this obnoxious disease will be most helpful and advantageous to them.

The appliance of this invention shown in FIGS. 10 to 15 has all the advantages of my invention shown in FIGS. 1 to 9 and provides in addition thereto the feature of the large gel compartment with the diaphragm wall which is formed in the single operation of molding the gasket body. To this is added the feature of improved means for connecting the drain end of the pouch to the gasket body, which means is also formed in the molding of the gasket body. These features make for many advantages with low cost of manufacture of the appliance and economy to the user.

Referring to the low cost of manufacture of my appliance, I will explain some further details. The gasket body may be molded of any of suitable synthetic plastics, such as rubber, silicone, polyethylene, polyproylene, polyvinyls, polyvinylidene chloride, nylon, cellulose compounds, polyesters, urethaus, epories, silicone, natural rubber, synthetic rubbers, and various copsolymers. I prefer to use polyethylene as the material for molding the gasket body of my invention, mainly because it has the right degree of elasticity to form a good snap-ring; it has the right degree of flexibility to conform to the patients's body; it has the right degree of hardness so that it will not break as some brittle plastics do when stretched or flexed; it is lighter in weight than most plastics; it is not soluble in water or fetal discharge; and finally it is lower in cost than most materials.

In the molding operation, I find that the most suitable machine is an injection molding machine. In molding the complete gasket body the mold is made in two halves with cavities to the form of the gasket proper, the snap-ring and hinge, the diaphragm, the plural portions, and the details of connecting the drain end of the pouch and the belt ends. The two halves of the mold are mounted into the injection molding machine which is then actuated to close the mold halves. The machine then injects hot plastic into the closed die through a small opening called a sprue hole. The injected molten plastic is about 350 degrees F. The next function is to cool the mold by a cold water jacket attached to the mold, reducing the temperature to about 125 degrees F. The plastic mold is now solid. The molding machine now opens the two halves of the die and a machine operator removes the molded gasket body. The time required for one complete molding operation is about 45 seconds. If I should want greater production I would make a mold die with a larger number of cavities and use a larger molding machine. The single mold machine can make 10 complete gasket bodies in about 1 minute. A single die cavity machine can make about 1,000,000 gasket bodies before it would require repairs.

With present day costs of labor and materials the cost of molding one gasket body will be about 25 cents each. For greater economy the cost of each gasket body could be about one half of this by making a mold die with four cavities which would make four gasket bodies each minute. However, since my gasket body is reuseable as described above, my appliance costs less to use than prior appliances which connect the pouch to the gasket by heat sealing and other methods requiring numerous individually manufactured parts. These heat sealed units are usually thrown away after each use. Furthermore, with my invention, new tubular pouches may be used with the gasket body at a cost of less than 5 center per pouch, as described above about replacing pouches.

A distinct advantage in the matter of low cost of manufacture, is the feature of molding the gasket body with plural portions integral therewith designed so that each such portion serves a different function, totaling the full function of the appliance. This is of particular value when compared with prior appliances having many separate parts requiring individual and special tooling to make each part, such, for example as metal gaskets, face plates, pouch-gasket sealing, pouch connectors using coiled metal springs, drain end connectors to belts, belt hooks, buckles, slides, etc.

And as a further advantage in the matter of low cost of manufacture is the fact that this enables me to offer to the market and patients a particularly improved appliance at a saving in cost to the patient and economies in the patient's use of my appliance.

To sum up the fundamentals of my invention, I am giving to the public and the world (after a limited period of exclusive rights to myself under our laws) a better appliance for the treatment of colostomy and the like which can be produced at a lower cost and advantage to the user than prior appliances for this use, and one which marks a distinct and beneficial advance in this art.

I claim:

1. An improved appliance for the treatment of colostomy and the like, comprising a pouch having a receiving end and a drain end, a gasket having plural portions formed into a unitary structure having an opening for reception of the stoma, one such portion forming an annular peripheral lip around the stoma opening at its outlet end, another such portion forming a ring member hinged to the gasket, the receiving end of the pouch adapted to be inserted by hand into the center of the ring member, the ring member adapted to be moved by hand on its hinge to a position in which it coacts with said lip and presses an annular portion of the receiving end of the pouch into annular engagement with said lip to secure the pouch to the gasket, another such portion forming spaced jaws, and still another such portion forming a clamping bar hinged to the gasket and adapted to be moved by hand on its hinge after the drain end of the pouch has been placed by hand between said jaws to clamp said drain end to the gasket with said drain end closed.

* * * * *